(12) United States Patent
Hanada et al.

(10) Patent No.: US 6,960,350 B2
(45) Date of Patent: Nov. 1, 2005

(54) ANTIFUNGAL FRAGRANCE COMPOSITION

(75) Inventors: Minoru Hanada, Hiratsuka (JP); Hisao Iwai, Hiratsuka (JP); Jun Fujigasaki, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 10/012,365

(22) Filed: Dec. 12, 2001

(65) Prior Publication Data

US 2002/0177621 A1 Nov. 28, 2002

(30) Foreign Application Priority Data

Dec. 12, 2000 (JP) .................................... 2000-376958

(51) Int. Cl.$^7$ ..................... A01N 25/08; A01N 25/34; A61K 7/46
(52) U.S. Cl. ..................... 424/404; 424/43; 424/46; 424/404; 424/405; 424/406; 424/408; 424/409; 424/411; 422/28; 422/32; 422/36; 428/34.1; 428/35.2; 428/35.4; 428/35.5; 428/35.7; 428/36.1; 428/36.2; 428/36.6; 512/2; 512/5; 512/20; 512/21; 512/22; 512/23; 512/24; 512/25; 512/26; 512/27; 514/957
(58) Field of Search ................. 424/404–406, 424/43, 46, 408, 409, 411; 422/28, 32, 36; 512/2, 5, 20–27; 521/2, 5, 20–27; 428/34.1–36.6; 514/957

(56) References Cited

U.S. PATENT DOCUMENTS

| | | | | |
|---|---|---|---|---|
| 4,515,909 A | * | 5/1985 | Sawano et al. | 523/102 |
| 4,582,635 A | * | 4/1986 | Furuuchi et al. | 252/522 |
| 4,966,754 A | * | 10/1990 | Purohit et al. | 424/195.1 |
| 5,306,707 A | * | 4/1994 | Burrell et al. | 512/2 |
| 6,133,228 A | * | 10/2000 | Pika et al. | 512/21 |
| 6,183,766 B1 | * | 2/2001 | Sine et al. | 424/405 |
| 6,344,218 B1 | * | 2/2002 | Dodd et al. | 424/605 |
| 6,455,086 B1 | * | 9/2002 | Trinh et al. | 426/321 |

FOREIGN PATENT DOCUMENTS

| | | |
|---|---|---|
| DE | 25 16 670 A | 10/1976 |
| EP | 0 451 889 A1 | 10/1991 |
| JP | 3-285993 A | 12/1991 |
| JP | 6-24952 A | 2/1994 |
| JP | 10-130115 A | 5/1998 |
| JP | 10-338630 A | 12/1998 |
| JP | 11-335219 A | 12/1999 |
| WO | 97/32474 A | 9/1997 |
| WO | 01/24769 A1 | 4/2001 |

OTHER PUBLICATIONS

Chemical Abstracts 118:35713, "Elimination of allergenic molds in dwellings. Antifungal properties of the vapors of geranium oil, cintronellol, geraniol and citral", Chaumont et al (1992).*
HCAPLUS 118: 143261, 1993.*
HCAPLUS 129: 105501, 1998.*
HCAPLUS 79: 57561, 1973.*
Nandi, B.; "Effect of some volatile aldehydes, ketones, esters and terpenoids on growth and development of fungi associated with wheat grains in the field and in storage"; *Journal of Plant Diseases and Protection*; vol. 84, No. 2, pp. 114–128; 1998.
Nandi, B.; "Grain preservative efficacies of some volatile compounds on wheat at different stages of infection by storage fungi"; *Phytophat. Z.*; vol. 92, pp. 251–261; 1978.
Moleyar, V. et al.; "Fungitoxicity of binary mixtures of citral, cinnamic aldehyde, menthol and lemon grass oil against *Aspergillus niger* and *Rhizopus stolonifer*"; *Lebensmitt. –Wiss. Technologies.*; vol. 2, No. 2, pp. 100–102; 1988.

* cited by examiner

*Primary Examiner*—Frederick Krass
(74) *Attorney, Agent, or Firm*—Kubovcik & Kubovcik

(57) ABSTRACT

An antifungal fragrance composition containing as its active ingredients: (a) at least one type of fragrance component selected from the group consisting of an aliphatic or aromatic aldehyde having 5 to 16 carbon atoms and an aliphatic or aromatic alcohol having 5 to 16 carbon atoms, and (b) at least one type of compound different from component (a) and selected from the group consisting of an aliphatic or aromatic aldehyde, an aliphatic or aromatic alcohol, acetal and ester that produces synergistic antifungal effects in the presence of said fragrance component (a). The present antifungal fragrance composition demonstrates antifungal activity by adding a small amount of oils and fragrant chemical products that have a minimal effect on the scent of the fragrance composition.

11 Claims, No Drawings

ANTIFUNGAL FRAGRANCE COMPOSITION

BACKGROUND OF THE INVENTION

1. Field of the Invention

The present invention relates to a fragrance composition having antifungal activity. An object of the present invention is to provide a highly safe antifungal fragrance composition that disperses a desired fragrance in a room, closet or shoe box in which it is placed while simultaneously inhibiting mold growth, thereby preventing contamination of wall surfaces, floor surfaces, shoe surfaces and so forth caused by mold.

2. Prior Art

One of the characteristics of harmful mold growth in homes in Japan is the high temperature and humidity that occur in summer. In contrast, during the winter, in the case of concrete housing complexes such as apartments, in particular, a major cause of harmful mold growth is the interior condensation of moisture due to thermal insulation resulting from internal thermal insulating methods. For these reasons, a large amount of mold is detected indoors in both the summer and winter. The types of mold isolated from rooms and bathrooms have been reported to vary according to the season, the region in which they were researched and other factors (Antibacterial and Antifungal Agents, Vol. 19, pp. 127–134 (1991); Antibacterial and Antifungal Agents, Vol. 28, pp. 421–426 (2000); etc.).

For example, *Wallemia, Aspergillus, Cladosporium, Penicillium* and other species of molds have been isolated from floor dust, while mold in the form of black stains present in the joints of bathroom tiles are said to be frequently caused by mold species such as *Cladosporium, Phoma, Aueroba-sidium* and *Ochroconis*. When such molds grow on wall surfaces, in closets or in shoe boxes, they can cause numerous problems such as mildew and other unpleasant odors, the creation of white, yellow, black or other stains, damage to wall surfaces or the resulting spores can become suspended in the room and cause allergies.

Antifungal agents are frequently used as a means of preventing such mold growth. However, many of the antifungal agents that are commonly used are aqueous sprays containing sodium hypochlorite as their main ingredient. Although these antifungal agents are easy to use since they can be rinsed off after use if used in locations involving the use of water such as in bathrooms or lavatories, in the case of ordinary rooms, closets and shoe boxes, etc., there are concerns over their strongly irritating odor and safety with respect to the human body. Moreover, there is also a risk of new moisture remaining after spraying and resulting following decomposition of the active ingredient such as sodium hypochlorite becoming a hotbed for mold growth.

Essential oils and their components, fragrant chemical products, have been widely known to have antibacterial and antifungal activity (Toru Asagoshi, Journal of the Society of Cosmetic Chemists of Japan, Vol. 34, pp. 25–46 (2000) and cited references therein), and have been shown in numerous reports to demonstrate activity not only in methods involving direct contact with test microorganisms, but also in the vapor state (Maruzzella, J. C. et al., American Perfumer and Aromatics 74 (Aug), 21–22 (1959); Shinobu Gocho, Antibacterial and Antifungal Agents, Vol. 20, p. 585 (1992); Tamio Nishimura, Aromatopia, 10, 60–63 (1995)).

Examples of patents describing antibacterial or antifungal activity demonstrated by essential oils and fragrant chemical products in the vapor state include Japanese Patent Publication No. Hei 3-77161 (a non-therapeutic antimicrobial), Japanese Unexamined Patent Publication No. Hei 6-24952 (a bacteriostatic aromatic agent for the bathroom), Japanese Unexamined Patent Publication No. Hei 10-108691 (an antimicrobial activity detection method), Japanese Unexamined Patent Publication No. Hei 10-338630 (a fungal infection and diffusion preventive agent using essential oil), Japanese Unexamined Patent Publication No. Hei 11-332534 (a antibacterial and bactericidal agent for food) and Japanese Unexamined Patent Publication No. Hei 11-335219 (a bactericidal agent for the refrigerator).

However, the antibacterial and antifungal activities of these fragrant components are not so potent, and when prepared in an amount that demonstrates activity, the characteristic aroma of the active ingredient becomes conspicuous. There are many cases in which the scent of the overall preparation is controlled by the aroma of the active ingredient, thereby making it difficult to generate antibacterial and antifungal activity while maintaining a specific scent (such as a citrus, fruity, woody or mint scent).

SUMMARY OF THE INVENTION

Therefore, the object of the present invention is to provide an antifungal fragrance composition that is able to demonstrate antifungal activity with addition of a small amount of oils and fragrant chemical products having a minimal effect on the scent of the fragrance composition.

As a result of conducting earnest research on the antibacterial activity and antifungal activity of fragrant vapor, the inventors of the present invention found that by mixing at least one type of fragrance component selected from the group consisting of aliphatic or aromatic aldehydes having 5 to 16 carbon atoms and aliphatic or aromatic alcohols having 5 to 16 carbon atoms, and at least one type of compound different from the fragrance component and selected from the group consisting of aliphatic or aromatic aldehydes, aliphatic or aromatic alcohols, acetals and esters, antibacterial activity or antifungal activity of the mixture of fragrances is synergistically enhanced. This activity can be demonstrated even when both components are mixed at low concentrations such as those at which activity is not demonstrated with the fragrance component alone, and consequently without disturbing the specific scent of the overall preparation, and thus they accomplished the present invention.

Namely, the present invention is:

1) an antifungal fragrance composition containing as its active ingredients: (a) at least one type of fragrance component selected from the group consisting of an aliphatic or aromatic aldehyde having 5 to 16 carbon atoms and aliphatic or aromatic alcohols having 5 to 16 carbon atoms, and (b) at least one type of compound different from the fragrance component (a) and selected from the group consisting of an aliphatic or aromatic aldehydes, aliphatic or aromatic alcohols, acetals and esters and which demonstrate synergistic antifungal effects in the presence of the above-mentioned fragrance component (a). The aliphatic or aromatic aldehydes and the aliphatic or aromatic alcohols useful as compound (b) preferably have 5 to 16 carbon atoms.

2) the antifungal fragrance composition described in 1) above, wherein the fragrance component (a) is selected from the group consisting of citral, citronellal, trans-2-hexenal, octyl aldehyde, trans-2-undecenal, 10-undecen-1-al, dimethyl tetrahydrobenzaldehyde, benzaldehyde, salicylic aldehyde, 3-phenylpropionic aldehyde, cumin aldehyde, furfural, geraniol, citronellol, 9-decen-1-ol, 1-decanol and eugenol;
3) the antifungal fragrance composition described in 1) or 2) above, wherein the component (b) demonstrating synergistic effects is citral, citronellal, trans-2-hexenal, octyl aldehyde, 1-nonanal, trans-2-undecenal, 10-undecen-1-al, dimethyl tetrahydrobenzaldehyde, benzaldehyde, salicylic aldehyde, 3-phenylpropionic aldehyde, cumin aldehyde, furfural, phenylacetaldehyde, anisaldehyde, geraniol, citronellol, 9-decen-1-ol, 1-decanol, thymol, eugenol, citral dimethylacetal (hereinafter abbreviated as citral DMA), citral diethylacetal (hereinafter abbreviated as citral DEA), cinnamic aldehydodimethylacetal (hereinafter abbreviated as cinnamic aldehyde DMA), or methyl salicylate;
4) a gel containing the antifungal fragrance composition according to any one of 1) to 3) above in an amount of 1 to 50% by weight;
5) a powder or granules containing the antifungal fragrance composition according to any one of 1) to 3) above in an amount of 1 to 60% by weight;
6) a liquid containing the antifungal fragrance composition according to any one of 1) to 3) above in an amount of 1 to 30% by weight in a liquid;
7) an antifungal fragrance composition package comprising the antifungal fragrance composition according to any one of 1) to 3) above, or the composition dissolved in a volatile solvent, in a gas permeable container;
8) the antifungal fragrance composition package described in 7) above, wherein the gas permeable container is a pouch-shaped object made of a laminate comprising a gas permeable thermoplastic resin on the inside and a gas permeable support on the outside;
9) the antifungal fragrance composition package described in 8) above, wherein the gas permeable support is a non-woven fabric;
10) an antifungal fragrance composition package comprising the antifungal fragrance composition according to any one of 1) to 3) above, or the composition dissolved in a volatile solvent, and a propellant in a spray can; and,
11) a method of inhibiting mold growth comprising: placing the antifungal fragrance composition package according to any one of 7) to 9) above at a selected location, and dispersing the components (a) and (b) in the antifungal fragrance composition contained in the package.

In the present invention, by combining the use of the fragrant component of the component (a) having antifungal activity with the component (b) demonstrating a synergistic effect on antifungal activity in the presence of the component (a), the amount of fragrant component (a) blended that demonstrates activity can be reduced to a much lower amount than in the case of using the component (a) alone. As a result, even in the case of blending into other fragrances, there are minimal effects on the other fragrances, thereby making it possible to provide an antifungal fragrance composition that maintains a desired aroma while exhibiting an extremely high degree of safety with respect to the human body.

DETAILED DESCRIPTION OF PREFERRED EMBODIMENTS

Examples of aliphatic or aromatic aldehydes that can be used as component (a) and component (b) in the present invention include citral, citronellal, trans-2-hexenal, octyl aldehyde, trans-2-undecenal, 10-undecen-1-al, dimethyl tetrahydrobenzaldehyde (Triplal), benzaldehyde, salicylic aldehyde, 3-phenylpropionic aldehyde, cumin aldehyde and furfural, as well as 1-nonanal, phenylacetaldehyde, cinnamic aldehyde, anisaldehyde, perill aldehyde and helional. In addition, acetals of these aldehydes such as dimethylacetals and diethylacetals can similarly also be used. Moreover, in addition to these fragrant chemical products, natural fragrances and essential oils containing these substances as their components can also be used.

Examples of aliphatic and aromatic alcohols that can be used as component (a) and component (b) in the present invention include geraniol, citronellol, decen-1-ol, 1-decanol and eugenol as well as thymol, isoeugenol, hinokitiol and perilla alcohol. Moreover, natural fragrances and essential oils containing these substances as their components can also be used.

Examples of acetals that can be used include citral DMA, citral DEA and cinnamic aldehyde DMA, while examples of esters that can be used include methyl salicylate.

Although the blending ratio of the component (a) and component (b) in the antifungal fragrance composition of the present invention differs according to the type of each component and cannot be unconditionally determined, normally a ratio of (a):(b)=1:0.01 to 50 is preferable. For example, in the case of component (a) being citral and component (b) being citronellal, about 1 to 20 parts by weight of citronellal should be blended relative to 1 part by weight of citral.

The antifungal fragrance composition of the present invention can be in the form of a gel, powder, granules, liquid and so forth. In the case of being in the form of a gel, although it is common to use a gelling agent, there are no restrictions on the gelling agent used. Examples of gelling agents that can be used include those formed from water-soluble high polymeric organic substances such as polyvinyl alcohol, polyethylene glycol, polyvinyl pyrrolidone, alginic acid, cellulose, starch, their derivatives or their salts, synthetic resin emulsions such as vinyl acetate resin emulsions and copolymer-based resin emulsions, e.g. those of vinyl acetate and vinyl chloride, aqueous emulsions such as rubber-based latex, gelling agents derived from naturally-occurring substances extracted from various animals, plants, algae and microorganisms such as carrageenan, agar, gelatin and pectin. Surfactants such as sodium stearate and sodium isostearate may be used to disperse and emulsify the antifungal fragrance component in the gel. In the case of being in the form of a gel, the gel may contain 1 to 50% by weight of the antifungal fragrance composition.

In addition, in the case of being in the form of a powder or granules, 1 to 60% by weight of the antifungal fragrance composition should be adsorbed or impregnated. Examples of the carrier of the powder or granules include silica gel, zeolite, calcium silicate, diatomaceous earth, activated charcoal, alumina, allophane and vermiculite.

In addition, the antifungal fragrance composition of the present invention may also be in the form of a liquid, and in this case, can be composed of a surfactant such as polyoxyethylene hardened castor oil or 1 to 40% by weight aqueous ethanol as the solubilizing agent of the antifungal fragrance component, antioxidant such as dibutylhydroxytoluene, ultraviolet absorber such as urocanic acid or oxybenzone and a pigment, etc., and the antifungal fragrance component should be blended at 1 to 30% by weight.

The present invention also provides an antifungal fragrance composition package that contains the above antifungal fragrance composition in a container. The antifungal fragrance composition is contained directly, dissolved in a volatile solvent such as alcohol, or directly as a liquid, or is in a gas permeable container when the composition is in the form of the above-mentioned gel, powder or granules. Examples of gas permeable containers that are used preferably include those in which laminated paper is formed into the shape of a pouch, the laminated paper being made by using a non-woven fabric composed of a gas permeable material for the support, and laminating onto the support a film having an inner surface of polyethylene film or other gas permeable, thermoplastic film.

In addition, the present invention can also provide an antifungal fragrance composition package in which the antifungal fragrance composition of the present invention is placed in a manual spray container either directly or after dissolving in a volatile solvent such as alcohol, or is charged into a spray can with a propellant such as LPG, dimethyl ether or liquefied carbon dioxide gas.

If the above antifungal fragrance composition package is placed in a location such as a room, closet or shoe box, together with the scent of the fragrance component being dispersed at those locations, mold growth is inhibited, thereby being able to prevent staining and soiling of wall surfaces, floor surfaces, inside of shoe boxes, shoe surfaces and so forth caused by mold.

EXAMPLES

The present invention will be described in more detail by way of the following examples, but the present invention is not limited in any way to these examples.

Example 1

Confirmation of Fragrant Vapor Antifungal Activity

The method of Gocho, et al. (Antibacterial and Antifungal Agents, Vol. 19, p. 511–515 (1991)) with a slight variation was carried out to confirm the activity of the fragrant vapor. Physiological saline containing 0.05% Tween-80 was added to a slant on which the test organism grew well, and a spore suspension was produced at $1 \times 10^6$ CFU (Colony Forming Units)/ml in accordance with ordinary methods. Potato dextrose agar (PDA: Nissui Pharmaceutical) was used for the medium. To begin with, 10 ml of sterile PDA was pipetted into a Petri dish and after it solidified, another 6 ml of PDA containing 1% of the above described spore suspension was overlaid and solidified to prepare the test agar plate. For the fragrance sample, if the sample is in the form of liquid at ordinary temperatures, 20 $\mu$l of liquid was directly impregnated into a paper disc (Advantech, diameter: 8 mm, thick material), while a 50% by weight ethanol solution was prepared for crystals or powder, and 40 $\mu$l of that solution was then impregnated into the paper disc. It should be noted that 40 $\mu$l of ethanol did not have an effect whatsoever on mold growth.

The test agar plate was placed inversely, and the paper disc impregnated with the fragrance sample was placed in the center of the cover of the agar plate, followed by incubating for 72 hours at 27° C. Evaluation was made based on the diameter (mm) of the mold growth inhibition zone. When mold growth was inhibited over the entire surface of the agar plate, the diameter of the growth inhibition zone was reported as >85 mm. At locations where mold grew outside the inhibition zone, the diameter of the spore formation inhibition zone and the degree of growth were recorded by comparing with a control. The molds used in the test are shown in Table 1, wherein these molds consist of mold species that are isolated at high frequencies from rooms and bath rooms. In addition, the antifungal activities of the fragrant vapor investigated are shown in Table 2.

TABLE 1

| Abbreviation | Fungi strain name |
| --- | --- |
| An-1 | *Aspergillus niger* IFO 9455 |
| Ap-1 | *Aureobasidium pullulans* IFO 6353 |
| Cc-1 | *Cladosporium cladosporioides* IFO 6348 |

TABLE 2

| Abbreviation of Fungi tested | An-1 | | | Ap-1 | | | Cc-1 | | |
| --- | --- | --- | --- | --- | --- | --- | --- | --- | --- |
| Fragrance name | IZ | SI | Growth | IZ | SI | Growth | IZ | SI | Growth |
| 3-Phenyl-propanal | >85 | | none | >85 | | none | >85 | | none |
| Benzaldehyde | >85 | | none | >85 | | none | >85 | | none |
| Citral | >85 | | none | >85 | | none | >85 | | none |
| Citral DEA | >85 | | sparse | >85 | | sparse | >85 | | sparse |
| Citral DMA | >85 | | none | >85 | | none | >85 | | none |
| 10-undecen-1-al | >85 | | none | >85 | | sparse | >85 | | sparse |
| Cumin aldehyde | >85 | | none | >85 | | none | >85 | | none |
| Furfural | >85 | | none | >85 | | none | >85 | | none |
| Perill aldehyde | >85 | | none | >85 | | none | >85 | | none |
| Salicylic aldehyde | >85 | | none | >85 | | none | >85 | | none |
| Trans-2-hexenal | >85 | | none | >85 | | none | >85 | | none |
| Trans-2-undecenal | >85 | | none | >85 | | none | >85 | | none |
| Octyl aldehyde | 10 | >85 | weak | >85 | | none | >85 | | none |
| 1-nonanal | 20 | | weak | >85 | | sparse | >85 | | sparse |
| Citronellal | 15 | | weak | >85 | | sparse | >85 | | sparse |
| Dimethyl-tetrahydro-benzaldehyde | 0 | | weak | >85 | | sparse | >85 | | sparse |
| Cinnamic aldehyde DMA | 35 | 45 | weak | 65 | | slight | 0 | | good |
| Anisaldehyde | 45 | 60 | good | 35 | 40 | good | >85 | | sparse |

TABLE 2-continued

| Abbreviation of Fungi tested | An-1 | | | Ap-1 | | | Cc-1 | | |
|---|---|---|---|---|---|---|---|---|---|
| Fragrance name | IZ | SI | Growth | IZ | SI | Growth | IZ | SI | Growth |
| Helional | 10 | 35 | good | 35 | | weak | 0 | | weak |
| Geraniol | 45 | 65 | good | 30 | 45 | good | 70 | | weak |
| Citronellol | 35 | 55 | good | 35 | | weak | 35 | | weak |
| 9-Decen-1-ol | >85 | | none | 65 | | weak | >85 | | none |
| 1-Decanol | 80 | | weak | 40 | | slight | 60 | | weak |
| Thymol | 70 | >85 | weak | >85 | | sparse | >85 | | sparse |
| Eugenol | 40 | 60 | good | 40 | 60 | good | 70 | | weak |
| Hinokitiol | 60 | | good | 70 | | good | 0 | | good |
| Perilla alcohol | 30 | 40 | good | 40 | | slight | 45 | | slight |
| Isoeugenol | 30 | 50 | good | 35 | 40 | good | 45 | 55 | good |
| Methyl salicylate | 40 | | weak | 65 | | weak | 0 | | good |

IZ: Diameter of growth inhibition zone (mm), SI: Diameter of spore formation inhibition zone (mm), Growth: Growth status outside the inhibition zone (Good: Substantially the same as the control, Weak: Somewhat weak growth, Slight: Even weaker growth, Sparse: Low growth density and weak colony growth, None: No growth observed. In addition, a result of "Sparse" for growth of IZ>85 mm indicates that although an inhibition zone was not formed, test organism growth was weak and sparse.)

Example 2

Confirmation of Synergistic Action

An agar plate prepared according to the method of Example 1 was used while using An-1 (*Aspergillus niger*) for the test fungi. To begin with, the amount of each fragrance alone that resulted in a growth inhibition zone of 0 to 30 mm for An-1 was determined, and when the amount of the fragrance was 10 μl or less, the fragrance was diluted using ethanol. 10 μl of the ethanol containing the Table 3 prescribed amount of the fragrance was impregnated into a paper disc. The test agar plate was placed inversely, and the paper disc impregnated with each fragrance alone and a paper disc simultaneously impregnated with two types of fragrances were placed in the center of the cover, followed by incubating for 72 hours at 27° C. and measuring the diameters of the resulting growth inhibition zones. When the combined use of two types of fragrances demonstrated an inhibition zone 20 mm or more larger than the sum of the diameters of the growth inhibition zones of each fragrance alone, the two fragrances were judged to demonstrate synergistic action. When the diameter of the combined growth inhibition zone was 20 mm or more smaller, the two fragrances were judged to demonstrate antagonistic action. When the diameter of the combined growth inhibition zone was intermediate to the above, the two fragrances were judged to demonstrate additive action. A portion of the results were divided into synergistic action, additive action and antagonistic action and shown in Table 3.

TABLE 3

| Sample name | Sample amount | IZ | SI | Growth | Evaluation result |
|---|---|---|---|---|---|
| A: Citral | 2 μl | 0 | 20 | weak | |
| B: Benzaldehyde | 10 μl | 15 | >85 | slight | |

TABLE 3-continued

| Sample name | Sample amount | IZ | SI | Growth | Evaluation result |
|---|---|---|---|---|---|
| A + B | 2 + 10 μl | >85 | — | none | Synergistic action |
| A: Dimethyl tetrahydro-benzaldehyde | 20 μl | 0 | >85 | weak | |
| B: Geraniol | 10 μl | 30 | 45 | weak | |
| A + B | 20 + 10 μl | >85 | — | none | Synergistic action |
| A: Octyl aldehyde | 20 μl | 10 | 35 | weak | |
| B: 9-Decen-1-ol | 0.5 μl | 0 | — | weak | |
| A + B | 20 + 0.5 μl | 15 | 30 | weak | Additive action |
| A: Trans-2-undecenal | 3 μl | 30 | >85 | slight | |
| B: Phenylacetaldehyde | 5 μl | 25 | 30 | good | |
| A + B | 3 + 5 μl | 35 | 65 | weak | Antagonistic action |

The meanings of the IZ, SI and growth columns are the same as those shown in Table 2.

The results obtained as in Example 2 with other combinations are shown in Tables 4 through 7 as combination examples of respective synergistic, additive and antagonistic actions for each fragrant chemical product (a). Those components (b) that demonstrate synergistic action for each fragrant component of component (a) in the present invention are the compound group shown in the "Synergistic Effect" column of these tables. It should be noted that in order to make the table smaller, combinations that have already been listed once are not listed in other columns of the tables. Thus, in the case, for example, eugenol of Table 7 is component (a), those compounds that demonstrate synergistic action can be found by looking at other fragrance names in the "Synergistic Effect" columns of Tables 4 through 7.

TABLE 4

| Fragrance component | Synergistic effect | Additive effect | Antagonistic effect |
|---|---|---|---|
| Citral | Citronellal, Trans-2-hexenal, Octyl aldehyde, | 3-Phenyl-propionic |

TABLE 4-continued

| Fragrance component | Synergistic effect | Additive effect | Antagonistic effect |
|---|---|---|---|
| | Trans-2-undecenal, 10-Undecen-1-al, Dimethyl tetrahydrobenzaldehyde, Benzaldehyde, Salicylic aldehyde, Cumin aldehyde, Furfural, 1-nonanal, Anisaldehyde, Perill aldehyde, Geraniol, Citronellol, 9-Decen-1-ol, 1-Decanol, Thymol, Eugenol, Citral DMA, Citral DEA, Cinnamic aldehyde DMA | aldehyde, Phenylacetaldehyde, Methyl salicylate | |
| Benzaldehyde | Citronellal, Trans-2-hexenal, Octyl aldehyde, Trans-2-undecenal, 10-Undecen-1-al, Dimethyl tetrahydrobenzaldehyde, 3-phenylpropionic aldehyde, Salicylic aldehyde, Cumin aldehyde, Furfural, 1-Nonanal, Phenylacetaldehyde, Anisaldehyde, Perill aldehyde, Geraniol, Citronellol, 1-Decanol, Thymol, Eugenol, Citral DMA, Citral DEA, Cinnamic aldehyde DMA, Methyl salicylate | | 9-Decen-1-ol |
| 10-Undecen-1-al | Citronellal, Octyl aldehyde, Trans-2-undecenal, Dimethyl tetrahydrobenzaldehyde, Salicylic aldehyde, Cumin aldehyde, 1-Nonanal, Phenylacetaldehyde, Perill aldehyde, Citronellol, 9-Decen-1-ol, 1-Decanol, Thymol, Eugenol, Citral DMA, Citral DEA, Cinnamic aldehyde DMA, Methyl salicylate | 3-Phenylpropionic aldehyde, Furfural, Trans-2-hexenal, Anisaldehyde, Geraniol | |

TABLE 5

| Fragrance component | Synergistic effect | Additive effect | Antagonistic effect |
|---|---|---|---|
| 3-Phenylpropanal | Citronellal, Trans-2-hexenal, Trans-2-undecenal, Dimethyl tetrahydrobenzaldehyde, Salicylic aldehyde, Citral DMA, Citral DEA | Octyl aldehyde, Cumin aldehyde, Furfural, Citronellol, 9-Decen-1-ol, 1-Decanol, Thymol, 1-Nonanal, Anisaldehyde, Perill aldehyde, Cinnamic aldehyde DMA, Eugenol | Geraniol |
| Furfural | Citronellal, Trans-2-hexenal, Octyl aldehyde, Trans-2-undecenal, Cumin aldehyde, Geraniol, Citronellol, Thymol | | |
| Trans-2-hexenal | Citral DEA, Cumin aldehyde, Perill aldehyde, Salicylic aldehyde, Thymol, Trans-2-undecenal, Octyl aldehyde, Cinnamic aldehyde DMA, Methyl salicylate, Phenylacetaldehyde, 1-Decanol, Eugenol, Anisaldehyde, Geraniol, Dimethyl tetrahydrobenzaldehyde, Citronellol | Citral DMA, 1-Nonanal, 9-Decen-1-ol | |
| Citronellal | Citral DMA, Citral DEA, Cinnamic aldehyde DMA, Methyl salicylate, Cumin aldehyde, Perill aldehyde, Salicylic aldehyde, Trans-2-undecenal, Octyl aldehyde, 1-Nonanal, Phenylacetaldehyde, Eugenol, Anisaldehyde, Geraniol, Dimethyl tetrahydrobenzaldehyde | Thymol, 1-Decanol, Citronellol | 9-Decen-1-ol |

TABLE 6

| Fragrance component | Synergistic effect | Additive effect | Antagonism effect |
|---|---|---|---|
| Octyl aldehyde | Cumin aldehyde, Perill aldehyde, Salicylic aldehyde, Trans-2-undecenal, Dimethyl tetrahydrobenzaldehyde | Thymol, 9-decen-1-ol, Anisaldehyde, Geraniol, 1-Decanol | Citronellol |
| Trans-2-undecenal | Citral DMA, Citral DEA, Cumin aldehyde, Perill aldehyde, Salicylic aldehyde, 1-Decanol, Geraniol, Citronellol | Cinnamic aldehyde DMA, Methyl salicylate | Phenylacetaldehyde, Eugenol |
| Dimethyl tetrahydrobenzaldehyde | Cumin aldehyde, Geraniol | Thymol, 1-Decanol | |
| Salicylic aldehyde | Cumin aldehyde, Thymol, 1-Decanol, Citronellol | | |
| Cumin aldehyde | Citral DEA, Geraniol, Cinnamic aldehyde DMA, Phenylacetaldehyde, 1-Decanol, Anisaldehyde, Citronellol | 9-Decen-1-ol | |
| Geraniol | 1-Nonanal | Thymol, 9-Decen-1-ol | Citronellol, Phenylacetaldehyde, Eugenol |

TABLE 7

| Perfume component | Synergistic effect | Additive effect | Antagonism effect |
|---|---|---|---|
| Citronellol | Citral DMA, Citral DEA, Perill aldehyde, Methyl salicylate | 1-Nonanal, 1-Decanol, Anisaldehyde | Thymol, 9-Decen-1-ol, Cinnamic aldehyde DMA, Phenylacetaldehyde, Eugenol |
| 9-Decen-1-ol | 1-Decanol | Thymol | |
| 1-Decanol | | Thymol, 1-Nonanal, Methyl salicylate, Phenylacetaldehyde, Eugenol | Cinnamic aldehyde DMA |

TABLE 7-continued

| Perfume component | Synergistic effect | Additive effect | Antagonism effect |
|---|---|---|---|
| Eugenol | | Thymol, Methyl salicylate | Phenylacetaldehyde, Anisaldehyde, Cinnamic aldehyde DMA |

Example 3

Production of Antifungal Fragrance Composition

Four types of prepared fragrances (antifungal fragrance compositions) were formulated based on two types of bases (containing neither the components (a) nor (b)) consisting of a citrus-scented base fragrance (citrus base) and floral-scented base fragrance (floral base) according to the results of Examples 1 and 2. The contents of their formulas are shown in Table 8 (values represent parts by weight).

TABLE 8

| | Example 3-1 | Comp. Ex. 1 | Example 3-2 | Comp. Ex. 2 |
|---|---|---|---|---|
| Citrus base | 695 | 695 | 0 | 0 |
| Floral base | 0 | 0 | 647 | 647 |
| Component (a) | | | | |
| Citral | 250 | 0 | 170 | 0 |
| 10-Undecen-1-al | 50 | 0 | 30 | 0 |
| Component (b) | | | | |
| Benzaldehyde | 0 | 0 | 150 | 0 |
| 1-Nonanal | 5 | 0 | 0 | 0 |
| 3-Phenylpropionic aldehyde | 0 | 0 | 3 | 0 |
| Ethanol (balance) | 0 | 305 | 0 | 353 |

Example 4

Antifungal Activity of Compounded Fragrances

The activities of the blended fragrances (antifungal fragrance compositions) prepared in Example 3 were confirmed using the method of Example 1. Those results are shown in Table 9. The amount of blended fragrance added to the paper discs was 20 µl each, and only the diameter of the inhibition zone (mm) is indicated for the results.

TABLE 9

| Fragrance | Fungi tested | | |
|---|---|---|---|
| compounded | An-1 | Ap-1 | Cc-1 |
| Example 3-1 | >85 | >85 | >85 |
| Comp. Example 1 | 0 | 0 | 0 |
| Example 3-2 | >85 | >85 | >85 |
| Comp. Example 2 | 0 | 0 | 0 |

As can be seen from Table 9, although the blended fragrances of Examples 3-1 and 3-2 containing the component (a) and the component (b) (active ingredients) exhibited potent activity against the three species of fungi tested, there was no antifungal activity observed for the bases prior to addition of active ingredients.

In addition, separate from the above, the aroma of the blended fragrances were evaluated in the manner described below. Namely, twenty male and female subjects were asked to smell the aromas of Example 3-1, Comparative Example 1, Example 3-2 and Comparative Example 3-2, evaluations were made based on the following evaluation criteria, and the resulting average scores were determined.

| Score | Evaluated Contents |
|---|---|
| 4 | Retained scent of comparative example |
| 3 | Nearly retained scent of comparative example |
| 2 | Slight difference from scent of comparative example |
| 1 | Large difference from scent of comparative example |

The average evaluation score of the prepared fragrance of Example 3-1 was 3.8, while that of the prepared fragrance of Example 3-2 was 3.1. The prepared fragrance of Example 3-1 acquired antifungal activity while retaining the aroma of Comparative Example 1. Although the prepared fragrance of Example 3-2 was observed to exhibit a change in scent, the difference was only slight.

Example 5

Preparation of Granular Aromatic Agents

Granular aromatic agents were prepared using the blended fragrances produced in Example 3. Granular types of aromatic agents were produced by using granular calcium silicate (florite, Tokuyama soda) and impregnating with 60% by weight of each blended fragrance of Example 3.

The granular aromatic agent containing the blended fragrance of Example 3-1 was referred to as Example 5–1, the granular aromatic agent containing the fragrance of Comparative Example 1 as Comparative Example 3, the granular aromatic agent containing the blended fragrance of Example 3-2 as Example 5-2, and the granular aromatic agent containing the fragrance of Comparative Example 2 as Comparative Example 4.

Example 6

Antifungal Activity of Granular Aromatic Agents

The granular aromatic agents were evaluated using a vinyl chloride container having an internal volume of 78 liters (inner diameter: 30 cm×110 cm, stainless steel lining). The test method was as described below. Strips of board cut to a length of 32 cm were grouped into the shape of a cross, four chains were suspended at a location 2 cm from the ends, and four levels of circular metal mesh having a diameter of 25 cm were suspended from the chains. The metal mesh of the first level was positioned 10 cm from the upper edge of the container, and the remaining metal mesh were located at heights of 25 cm, 65 cm and 105 cm from the upper edge of the container. One each of the agar plates of the same fungi tested used in Example 1 was placed on each metal mesh. The aromatic agents of the present example were used after weighing out so that the amount of active ingredient contained therein was 10 µg/cm$^3$. In other words, the total amount of active ingredients shown in Table 8 was calculated to be 780 mg (10 µg/cm$^3$) from the scenting rate of the aromatic agents. The weights of the aromatic agents were 4.62 g in Example 5-1 and 3.68 g in Example 5-2. In the comparative examples, aromatic agents were used at the same weights as in the respective examples. Each aromatic agent was wrapped in tissue paper and respectively placed in the center of the metal mesh of the second level. This was done to confirm whether or not the vapor is dispersed upward as well.

After positioning the aromatic agents and agar plates on the metal mesh, they were placed in the container, the opening of the container was wrapped twice and then incubated for 3 days at 27° C. The growth status of the fungi tested on each agar plate was compared with a control. The results of Example 6 are shown in Table 10.

TABLE 10

|  | Example 5-1 | Comp. Ex. 3 | Example 5-2 | Comp. Ex. 4 |
| --- | --- | --- | --- | --- |
| First level | No growth | Growth | No growth | Growth |
| Second level | No growth | Growth | No growth | Growth |
| Third level | No growth | Growth | No growth | Growth |
| Fourth level | No growth | Growth | No growth | Growth |

The granular aromatic agents of Examples 5-1 and 5-2 completely inhibited growth of the fungi tested (An-1, Ap-1 and Cc-1) on agar plates placed at the height of the fourth level. In contrast, the fungi tested on the agar plates placed together with the granular aromatic agents of Comparative Examples 3 and 4 exhibited growth similar to that of the control, and the granular aromatic agents of Comparative Example 3 and 4 were not observed to demonstrate antifungal activity.

Example 7

Preparation of Water-Soluble Gel Type Aromatic Agents

Gelatinous aromatic agents were prepared using the blended fragrances produced in Example 3 according to the formulas indicated below.

| Formula of Water-Soluble Gel Type Aromatic Agents | |
| --- | --- |
| κ-Carrageenan | 2.0% |
| Locust bean gum | 0.4% |
| Polyethylene glycol | 3.0% |
| Calcium chloride | 0.4% |
| Antiseptic (methylparaben) | 0.1% |
| Blended fragrance of Example 3 | 5.0% |
| Tween-80 | 0.5% |
| Water | 88.6% |

The gelatinous aromatic agent containing the blended fragrance of Example 3-1 was referred to as Example 7-1, the gelatinous aromatic agent containing the fragrance of Comparative Example 1 as Comparative Example 5, the gelatinous aromatic agent containing the blended fragrance of Example 3-2 as Example 7-2, and the gelatinous aromatic agent containing the fragrance of Comparative Example 2 as Comparative Example 6.

Example 8

Antifungal Activity of Gelatinous Aromatic Agents

The antifungal activity of the gelatinous aromatic agents was investigated using the same method as Example 6. The weight of the gel used was 51.15 g in Example 7-1 and 44.19 g in Example 7-2. The same weights of gel were also used in each of the comparative examples. The gel was placed in a wide-mouth bottle having an opening diameter of 32 mm, and placed in the center of the metal mesh on the second level in the same manner as Example 6. The antifungal activity of the other gelatinous aromatic agents was investigated in the same manner as Example 6. Those results are shown in Table 11.

TABLE 11

|  | Example 7-1 | Comp. Ex. 5 | Example 7-2 | Comp. Ex. 6 |
| --- | --- | --- | --- | --- |
| First level | No growth | Growth | No growth | Growth |
| Second level | No growth | Growth | No growth | Growth |
| Third level | No growth | Growth | No growth | Growth |
| Fourth level | No growth | Growth | No growth | Growth |

The gelatinous aromatic agents of Examples 7-1 and 7-2 completely inhibited growth of the fungi tested (An-1, Ap-1 and Cc-1) on agar plates placed at the height of the fourth level in the same manner as Example 6. In contrast, the gelatinous aromatic agents of Comparative Examples 5 and 6 were not observed to have antifungal activity.

As has been described in detail above, the antifungal fragrance composition of the present invention contains as its active ingredients (a) at least one type of fragrance component selected from the group consisting of citral, citronellal, trans-2-hexenal, octyl aldehyde, trans-2-undecenal, 10-undecen-1-al, dimethyl tetrahydrobenzaldehyde, benzaldehyde, salicylic aldehyde, 3-phenylpropionic aldehyde, cumin aldehyde, furfural, geraniol, citronellol, 9-decen-1-ol, 1-decanol and eugenol, and (b) at least one type of compound that demonstrates synergistic effects in the presence of the above fragrance component selected from the group consisting of aliphatic or aromatic aldehydes, aliphatic or aromatic alcohols, acetal and ester, thereby making it possible to reduce the contained amounts of active ingredients to a lower amount than in the case of using each alone.

Consequently, an antifungal fragrance composition can be produced that retains a desired aroma which has an extremely high degree of safety with respect to the human body. In addition, the blending of these antifungal fragrance compositions with aromatic agents and so forth makes it possible to inhibit the propagation of mold in rooms, closets or shoe boxes, thereby preventing mold from soiling wall surfaces, floor surfaces, shoe surfaces and so forth, or preventing allergies caused by dispersed mold spores.

What is claimed is:

1. An antifungal fragrance composition, consisting of, as its sole active antifungal ingredients: (a) at least one fragrance selected from the group consisting of dimethyl tetrahydrobenzaldehyde, benzaldehyde, salicylic aldehyde, 3-phenylpropionic aldehyde, cumin aldehyde and furfural, and (b) at least one fragrance selected from the group consisting of geraniol, citronellol, 9-decen-1-ol and 1-decanol, the ratio of (a):(b) being 1:0.01 to 50 by weight, wherein components (a) and (b) provide an antifungal effect which is greater than additive when said composition is applied in an effective amount to a location containing fungus.

2. A gel containing the antifungal fragrance composition according to claim 1 in an amount of 1 to 50% by weight of the gel.

3. A powder or granules containing the antifungal fragrance composition according to claim 1 adsorbed or impregnated at 1 to 60% by weight of the powder or granules.

4. A liquid containing the antifungal fragrance composition according to claim 1 in an amount of 1 to 30% by weight of the liquid.

5. An antifungal fragrance composition package comprising the antifungal fragrance composition according to claim 1, or said antifungal fragrance composition dissolved in a volatile solvent, in a gas permeable container.

6. The antifungal fragrance composition package according to claim 5, wherein said gas permeable container is a pouch-shaped object made of a laminate comprising a gas permeable thermoplastic resin on the inside and a gas permeable support on the outside.

7. The antifungal fragrance composition package according to claim 6, wherein the gas permeable support is a non-woven fabric.

8. An antifungal fragrance composition package comprising the antifungal fragrance composition according to claim 1, or said antifungal fragrance composition dissolved in a volatile solvent, and a propellant in a spray can.

9. A method of inhibiting mold growth comprising: placing the antifungal fragrance composition package according to claim 1 at a location containing fungus selected from the group consisting of *Aspergillus niger*, *Auerobasidium* and *Cladosporium* cladosporioides, and dispersing the components (a) and (b) in the antifungal fragrance composition at said location.

10. A method of inhibiting mold growth comprising: placing the antifungal fragrance composition package according to claim 6 at a location containing fungus, and dispersing the components (a) and (b) in the antifungal fragrance composition contained in said package at said location.

11. A method of inhibiting mold growth comprising: placing the antifungal fragrance composition package according to claim 7 at a location containing fungus selected from the group consisting of *Aspergillus niger*, *Auerobasidium* and *Cladosporium* cladosporioides, and dispersing the components (a) and (b) in the antifungal fragrance composition contained in said package at said location.

* * * * *